(12) United States Patent
Tsai et al.

(10) Patent No.: US 6,667,297 B2
(45) Date of Patent: *Dec. 23, 2003

(54) METHODS FOR TREATING NEUROPSYCHIATRIC DISORDERS

(75) Inventors: Guochuan Tsai, Cambridge, MA (US); Joseph Coyle, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/196,686

(22) Filed: Jul. 15, 2002

(65) Prior Publication Data

US 2002/0193429 A1 Dec. 19, 2002

Related U.S. Application Data

(63) Continuation of application No. 09/834,351, filed on Apr. 13, 2001, now Pat. No. 6,420,351, which is a continuation of application No. 09/291,296, filed on Apr. 14, 1999, now Pat. No. 6,228,875.
(60) Provisional application No. 60/081,645, filed on Apr. 14, 1998.

(51) Int. Cl.$^7$ .................. A61K 31/66; A61K 31/42; A61K 31/195

(52) U.S. Cl. .................. 514/119; 514/380; 514/561

(58) Field of Search ................ 514/119, 380, 514/561

(56) References Cited

U.S. PATENT DOCUMENTS

| | | | |
|---|---|---|---|
| 3,873,722 A | 3/1975 | Smythies | |
| 5,015,740 A | 5/1991 | Kennis et al. | |
| 5,051,448 A | 9/1991 | Shashoua | |
| 5,061,721 A | 10/1991 | Cordi et al. | |
| 5,112,863 A | 5/1992 | Hashimoto et al. | 514/534 |
| 5,187,171 A | 2/1993 | Cordi | |
| 5,260,324 A | 11/1993 | Cordi et al. | |
| 5,468,763 A | 11/1995 | Cordi et al. | |
| 5,482,967 A | 1/1996 | Natsugari et al. | 514/457 |
| 5,633,281 A | 5/1997 | Teall et al. | 514/567 |
| 5,837,730 A | 11/1998 | Javitt | |
| 5,854,286 A | 12/1998 | Javitt et al. | |
| 6,162,827 A | 12/2000 | Javitt | 514/561 |
| 6,228,875 B1 * | 5/2001 | Tsai et al. | 514/380 |
| 6,355,681 B2 | 3/2002 | Javitt | 514/561 |
| 6,361,957 B1 | 3/2002 | Javitt | 435/7.1 |
| 2002/0161048 A1 | 10/2002 | Javitt | 514/561 |

FOREIGN PATENT DOCUMENTS

| | | | |
|---|---|---|---|
| DE | 41 17 629 | 12/1992 | |
| DE | 41 17 629 A1 | 12/1992 | A61K/31/685 |
| EP | 0 387 867 | 9/1990 | |
| EP | 0 387 867 A1 | 9/1990 | A61K/31/42 |
| EP | 0 432 039 A2 | 6/1991 | A61K/31/195 |
| EP | 0 652 012 A1 | 5/1995 | |
| EP | 0 696 586 A1 | 2/1996 | C07D/307/52 |
| HU | P9200192 A | 1/2003 | |
| JP | 55 020747 A | 2/1980 | A61K/31/19 |
| JP | 8-26986 | 1/1996 | |
| JP | 08 026986 A | 1/1996 | A61K/31/215 |
| RU | 2096044 C1 | 11/1997 | |
| WO | WO 89/05144 | 6/1989 | A61K/31/42 |
| WO | WO 97/20552 | 6/1997 | A61K/31/95 |
| WO | WO 97/20553 | 6/1997 | A61K/31/195 |

OTHER PUBLICATIONS

Baxter et al. "D–Cycloserine, a Novel Cognitive Enhancer, Improves Spatial Memory in Aged Rats" *Neurobiology of Aging* 15(2):207–213 (1994).

Baxter et al. "Modulation of the NMDA Receptor Complex by D–Cycloserine" *CNS Drug Reviews* 1(1):74–90 (1995).

Chessell et al. "D–Cycloserine, a putative cognitive enhancer, facilitates activation of the N–methyl–D–aspartate receptor–ionophore complex in Alzheimer brain" *Brain Research* 565:345–348 (1991).

Contreras "D–Serine Antagonized Phencyclidine– and MK–801–Induced Stereotyped Behavior and Ataxia" *Neuropharmacology* 29(3):291–293 (1990).

Fishkin et al. "D–Cycloserine Attenuates Scopolamine–Induced Learning and Memory Deficits in Rats" *Behavioral and Neural Biology* 59:150–157 (1993).

Francis et al. "A Glycine Site as Therapeutic Target$^a$" *Annals New York Academy of Sciences* 184–188 (1991).

Goff et al. "D–Cycloserine Added to Clozapine for Patients with Schizophrenia" *Am J. Psychiatry* 153(12):1628–1630 (1996).

Goff et al. "Dose–Finding Trial of D–Cycloserine Added to Neuroleptics for Negative Symptoms in Schizophrenia" *Am J. Psychiatry* 152(8):1213–1215 (1995).

Javitt et al. "Glycyldodecylamide, a phencyclidine behavioral antagonist, blocks cortical glycine uptake: implications for schizophrenia and substance abuse" *Psychopharmacology* 129:96–98 (1997).

Javitt et al. "Reversal of Phencyclidine–Induced Hyperactivity by Glycine and the Glycine Uptake Inhibitor Glycylododecylamide" *Neruopsychopharmacology* 17(3):202–204 (1997).

(List continued on next page.)

*Primary Examiner*—Raymond Henley, III
(74) *Attorney, Agent, or Firm*—Fish & Richardson P.C.

(57) ABSTRACT

The invention provides methods for treating neuropsychiatric disorders such as schizophrenia, Alzheimer's Disease, autism, depression, benign forgetfulness, childhood learning disorders, close head injury, and attention deficit disorder. The methods entail administering to a patient diagnosed as having a neuropsychiatric disorder a pharmaceutical composition containing (i) a therapeutically effective amount of D-alanine (or a modified form thereof), provided that the composition is substantially free of D-cycloserine, and/or (ii) D-serine (or a modified form thereof), and/or (iii) 105 to 500 mg of D-cycloserine (or a modified form thereof), and/or (iv) N-methylglycine (or a modified form thereof).

59 Claims, No Drawings

OTHER PUBLICATIONS

Matsuoka et al. "D–Cycloserine, a Partial Agonist at the Glycine Site Coupled to N–Methyl–D–aspartate Receptors, Improves Visual Recognition Memory in Rhesus Monkeys" *The Journal of Pharmacology and Experimental Therapeutics* 278(2):891–897 (1996).

Nilsson et al. "Glycine and D–serine decrease MK–801–induced hyperactivity in mice" *J. Neural Transm* 104:1195–1205 (1997).

Nishikawa et al. "PCP–induced abnormal behaviour and c–fos gene expression in the brain as indices for neuroleptic–resistant symptoms of schizophrenia" *Folia Pharmacologia Japonica* 108(1):53P–58P (1996) Abstract.

Papp et al. "Antidepressant–like effects of 1–aminocyclopropanecarboxylic acid and D–cycloserine in an animal model of depression" *European Journal of Pharmacology* 316:145–151 (1996).

Prous et al. "D–Cycloserine" *Drugs of the Future* 19(11):988–991 (1994).

Ramakers et al. "The Impaired Long–Term Potentiation in the CA1 Field of the Hippocampus of Cognitive Deficient Microencephalic Rats is Restored by D–Serine" *Neuroscience* 54(1):49–60 (1993).

Ramakrishna et al. "Betaine reverses toxic effects of aluminium: Implications in Alzheimer's disease (AD) and AD–like pathology" *Current Science* 75(11):11531156 (1998).

Riekkinen et al. "The effects of D–cycloserine on cognition in experimental models of Alzheimer's disease" *Neurology* 43(4):A292 (1993) Abstract.

Rimland "Dimethylglycine (DMG), a nontoxic metabolite and autism" *Autism Research Review International* 4(2):3 (1990).

Schuster et al. "D–Cycloserine reverses the working memory impairment of hippocampal–lesioned rats in a spatial learning task" *European Journal of Pharmacology* 224:97–98 (1992).

Sirviö et al. "D–Cycloserine, a modulator of the N–methyl–D–aspartate receptor, improves spatial learning in rats treated with muscarinic antagonist" *Neuroscience Letters* 146:215–218 (1992).

Tanii et al. "Effects of allosteric agonists for NMDA receptor and their derivatives on PCP–induced abnormal behaviours in rat" *The Japanese Journal of Psychiatry and Neurology* 44(4):790 (1990).

Tanii et al. "Stereoselective Antagonism by Enantiomers of Alanine and Serine of Phencyclidine–Induced Hyperactivity, Stereotypy and Ataxia in the Rat[1]" *The Journal of Pharmacology and Experimental Therapeutics* 269(3):1040–1048 (1994).

Temple et al. "Chronic, post–injury administration of D–cycloserine, an NMDA partial agonist, enhances cognitive performance following experimental brain injury" *Brain Research* 741:246–251 (1996).

Vamvakides "Nootropic activity of glycinergic derivatives in relation to their dualistic effects on cerebral monoamines" *Boll Chim Farma* 133(6):369–373 (1994) Abstract.

van Berckel et al. "Efficacy and Tolerance of D–Cycloserine in Drug–Free Schizophrenic Patients" *Society of Biological Psychiatry* 40:1298–1300 (1996).

Barnes et al.; "A Rating Scale for Drug–Induced Akathisia"; *British Journal of Psychiatry* 154; pp. 672–676; 1989.

Bart et al.; "Efficacy and Tolerance of D–Cycloserine in Drug–Free Schizophrenic Patients"; *Biological Psychiatry* 40; pp. 1298–1300; 1996.

Baxter et al.; "D–Cycloserine, a Novel Cognitive Enhancer, Improves Spatial Memory in Aged Rats"; *Neurobiology of Aging* 15(2); pp. 207–213; 1994.

Baxter et al.; "Modulation of the NMDA Receptor Complex by D–Cycloserine"; *CNS Drug Reviews* 1(1); pp. 74–90; 1995.

Chessell et al.; "D–Cycloserine, a putative cognitive enhancer, facilitates activation of the N–methyl–D–aspartate receptor–ionophore complex in Alzheimer brain"; *Brain Research* 565; pp. 345–348; 1991.

Contreras; "D–Serine Antagonized Phencyclidine– and MK–801–Induced Stereotyped Behavior and Ataxia"; *Neuropharmacology* 29(3); pp. 291–293; 1990.

"D–Cycloserine"; *Drugs of the Future*19(11); pp. 988–991; 1994.

D'Souza et al., "Glycine Site Agonists of the NMDA Receptor: A Review" *CNS Drug Reviews* 1,2:227–260 (1995).

Fishkin et al.; "D–Cycloserine Attenuates Scopolamine–Induced Learning and Memory Deficits in Rats"; *Behavioral and Neural Biology* 59; pp. 150–157; 1993.

Francis et al.; "A Glycine Site As Therapeutic Target[a]"; Institute of Neurology, Miriam Marks Department of Neurochemistry; London, WC1N, 1PJ, United Kingdom; pp. 184–188 (No date available).

Goff et al.; "D–Cycloserine Added to Clozapine for Patients With Schizophrenia"; *Am. J. Psychiatry* 153: 12; pp. 1628–1630; Dec. 1996.

Goff et al.; "Dose–Finding Trial of D–Cycloserine Added to Neuroleptics for Negative Symptoms in Schizophrenia"; *Am. J. Psychiatry* 152(8); pp. 1213–1215 (No date available).

Javitt et al.; "Glycyldodecylamide, a phencyclidine behavioral antagonist, blocks cortical glycine uptake: implications for schzophrenia and substance abuse"; *Psychopharmacology* 129; pp. 96–98; 1997.

Javitt et al.; "Reversal of Phencyclidine–Induced Hyperactivity by Glycine and the Glycine Update Inhibitor Glycyldodecylamide"; *Neuropsychopharmacology* 17(3); pp. 202–204; 1997.

Kay et al.; "The Positive and Negative Syndrome Scale (PANSS) for Schizophrenia"; *Schizophrenia Bulletin National Institute of Mental Health*; 13(1); pp. 261–276; 1987.

Kirkpatrick et al.; "The Schedule for the Deficit Syndrome: An Instrument for Research in Schizophrenia"; *Psychiatry Research*, vol. 30; pp. 119–123 (No date available).

Lindenmayer et al.; "Five–Factor Model of Schizophrenia Initial Validation"; *The Journal of Nervous and Mental Disease*; 182(11); pp. 631–638; 1994.

Lingjaerde et al.; "The UKU side effects rating scale"; *Scandinavian Society of Psychopharmacology Committee of Clinical Investigations (UKU)*; pp. 81–94 (No date available).

Malhotra et al., "NMDA receptor function and human cognition the effects of ketamine in healthy volunteers" *Neuropsychopharmacology* 14,5:301–307 (1996).

Matsuoka et al.; "D–Cycloserine, a Partial Agonist at the Glycine Site Coupled to N–Methyl–D–aspartate Receptors, Improves Visual Recognition Memory In Rhesus Monkeys"; *The Journal of Pharmacology and Experimental Therapeutics* 278(2); pp. 891–897; 1996.

McKhann et al.; "Clinical diagnosis of Alzheimer's disease: Report of the NINCDS–ADRDA Work Group under the auspices of Department . . . " *Neurology*, vol. 34; Jul. 1984; pp. 939–944.

Morrison; "Organic Chemistry"; Chapter 23; pp. 822–823 (No date available).

Nilsson et al., "Glycine and D–serine decrease MK–801–induced hyperactivity in mice"; *J. Neural. Transm* 104; pp. 1195–1205; 1997.

Papp et al.; "Antidepressant–like effects of 1–aminocyclo-propanecarboxylic acid and D–cycloserine in an animal model of depression"; *European Journal of Pharmacology* 316; pp. 145–151; 1996.

Patent Abstract; XP–002117995; Nishikawa et al.; "PCP–induced abnormal behavior and c–fos gene expression in the brain as indices for neuroleptic–resistant symptoms of schizophrenia"; *Folia Pharmacologica Japonica*; 1996.

Patent Abstract; XP–002117997; JP08026986; "Anti–phencyclidine drugs contain D–serine esters of formula (I) or their salts as active agents"; 1996.

Ramakers et al.; "The Impaired Long–Term Potentiation in the CA1 Field of the Hippocampus of Cognitive Deficient Microencephalic Rats is Restored by D–Serine"; *Neuroscience 54(1)*; pp. 49–60; 1993.

Ramakrishma et al.; "Betaine reverses toxic effects of aluminum: Implications in Alzheimer's disease (AD) and AD–like pathology"; *Current Science* 75(11); pp. 1153–1156; Dec. 1998.

Riekkinen et al.; "The Effects of D–Cycloserine on Cognition in Experimental Models of Alzheimer's Disease"; *Neurology* 43(4); p. A292, Abstract XP–0021178979 (No date available).

Rimland; "Dimethylglycine (DMG), a nontoxic metabolite, and autism"; *Editor's Notebook*; XP–002117993; 1 page (No date available).

Rockstroh et al.; "Effects of the Novel NMDA receptor antagonist SDZ EAA 494 on memory and attention in humans" *Psychopharmacology* 124:261–266 (1996).

Rosen et al.; "A new rating scale for Alzheimer's Disease"; *The American Journal of Psychiatry*; vol. 141, No. 11, Nov. 1984; pp. 1356–1364.

Russel; "A Multiple scoring method for the assessment of complex memory functions"; *Journal of Consulting and Clinical Psychology*, 43(6); pp. 800–809; Dec. 1975.

Schuster et al.; "D–Cycloserine reverse the working memory impairment of hippocampal–lesioned rats in a spatial learning task"; *European Journal of Pharmacology* 224; pp. 97–98; 1992 (No date available).

Simpson et al. "A Rating Scale for Extrapyramidal Side Effects"; 1970, *Acta Psychiatr.Scand. Suppl.* 212:11–19.

Sirvio et al.; "D–Cycloserine, a modulator of the N–methyl–D–aspartate receptor, improves spatial learning in rats treated with muscarinic antagonist"; *Neuroscience Letters 146*; pp. 215–218; 1992.

Tanii et al.; "Effects of Allosteric Agonists for NMDA Receptor and Their Derivatives on PCP–Induced Abnormal Behaviors in Rat"; National Institute of Neuroscience, NCNP, Kodaira; XP–002117991; 44(4); Dec. 1990.

Tanii et al.; "Stereoselective Antagonism by Enantiomers of Alanine and Serine of Phencyclidine–Induced Hyperactivity, Stereotypy and Ataxia in the Rat"; *The Journal of Pharmacology and Experimental Therapeutics* 269(3); pp. 1040–1048; 1994.

Temple et al., "Chronic, post–injury administration of D–cycloserine, an NMDA partial agonist, enhances cognitive performance following experimental brain injury"; *Brain Research* 741; pp. 246–251; 1996.

van Berckel BN et al.; "Efficacy and tolerance of D–cycloserine in drug–free schizophrenic patients", *Biol. Psychiatry* 40(12); pp. 1298–1300; Dec. 15, 1996.

XP–002117994; Journal Article Abstract; "Nootropic activity of glycinergic derivatives in relation to their dualistic effects on cerebral monoamines"; *Boll. Chim. Farm.* 133(6); pp. 369–373; Jun. 1994.

Cascella et al. "D–Cycloserine adjuvant therapy to conventional neuroleptic treatment in schizophrenia: an open–label study" *Journal of Neural Transmission* 95:10–111 (1994).

Crane "Cycloserine as an Antidepressant Agent" *The American Journal of Psychiatry* 115:1025–1026 (159) (1959).

Cutler et al. "The Tolerability and Efficacy of Cycloserine in Alzheimer's Disease" *Am. Coll. Neuropsychopharmacol.* Annual Meeting 1994 Puerto Rico.

Falk et al. "A Case Series of D–Cycloserine Added to Donepezil in the Treatment of Alzheimer's Disease" *J. Neuropsychiatry Clin Neurosci* 14(4):466–467 (2002).

Hashimoto et al. "D–Alanine inhibits methamphetamine–induced hyperactivity in rats" *European Journal of Pharmacology* 202:105–107 (1991).

Kumashiro et al. "Free D–serine in post–mortem brains and spinal cords of individuals with and without neuropsychiatric diseases" *Brain Res.* 681(1–2):117–125 (1997).

Leiderman et al. "Preliminary Investigation of High–Dose Oral Glycine in Serum Levels and Negative Symptoms in Schizophrenia: An Open–Label Trial" *Biological Psychiatry* 39(3):213–215 (1996).

Monahan et al. "Characterization of a [$^3$H]Glycine Recognition Site as a Modulatory Site of the N–Methyl–D–Aspartate Receptor Complex" *Journal of Neurochemistry* 53(2):370–375 (1989).

Randolph et al. "D–Cycloserine Treatment of Alzheimer Disease" *Alzheimer Disease and Associate Disorders* 8(3):198–205 (1994).

Simeon et al. "D–Cycloserine Therapy of Psychosis by Symptom Provocation" *Comprehensive Psychiatry* 11:80–88 (1970).

Tanii et al. "Stereoselective inhibition by D– and L–alanine of phencyclidine–induced locomotor stimulation in the rat" *Brain Research* 563:281–284 (1991).

Tsai et al. "A Preliminary Study of D–Cycloserine Treatment in Alzheimer's Disease" *The Journal of Neuropsychiatry* 10(2):224–226 (1998).

Tsai et al. Improved cognition in Alzheimer's Disease with Short–Term D–Cycloserine Treatment *Am. J. Psychiatry* 156(3):467–469 (1999).

* cited by examiner

METHODS FOR TREATING NEUROPSYCHIATRIC DISORDERS

CROSS-REFERENCE TO RELATED APPLICATION

This application is a continuation of U.S. patent application Ser. No. 09/834,351, filed Apr. 13, 2000, now U.S. Pat. No. 6,420,351, which is a continuation of U.S. patent application Ser. No. 09/291,296, filed Apr. 14, 1999, now U.S. Pat. No. 6,228,875, issued May 8, 2001, which claims the benefit of provisional application U.S. Ser. No. 60/081,645, filed Apr. 14, 1998, expired.

BACKGROUND OF THE INVENTION

Schizophrenia, Alzheimer's Disease, autism, depression, benign forgetfulness, childhood learning disorders, close head injury, and attention deficit disorder are examples of neuropsychiatric disorders. Autism, for example, is a developmental mental disorder characterized by autistic behavior, social failure, and language delay. Alzheimer's Disease is a form of dementia that typically involves progressive mental deterioration, manifested by memory loss, confusion, and disorientation. Alzheimer's Disease typically is treated by acetylcholine esterase inhibitors such as tacrine hydrochloride or donepezil. Attention Deficit Disorder is a disorder that is most prevalent in children and is associated with increased motor activity and a decreased attention span. Attention Deficit Disorder commonly is treated by administration of psychostimulants such as Ritalin or Dexedrin. Depression is a clinical syndrome that includes a persistent sad mood or loss of interest in activities, which persists for at least two weeks in the absence of treatment. Conventional therapeutics include serotonin uptake inhibitors (e.g., PROZAC™), monoamine oxidase inhibitors, and tricyclic antidepressants.

The term schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates.

Conventional antipsychotic drugs, which act on the dopamine $D_2$ receptor, can be used to treat the positive symptoms of schizophrenia, such as delusion and hallucination. In general, conventional antipsychotic drugs and the new a typical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

SUMMARY OF THE INVENTION

The invention derives from the discovery that neuropsychiatric disorders characterized by a deficit in neurotransmission via the NMDA receptor can be alleviated by a compound that acts as an agonist of the glycine site on the NMDA receptor or an inhibitor of glycine uptake. The compound is either a partial agonist such as D-cycloserine, which can be used at a dosage of 105–500 mg, or a full agonist (e.g., D-serine or D-alanine) that is selective for the NMDA receptor (compared to the inhibitory glycine receptor and other receptors), or a glycine uptake inhibitor (e.g., N-methylglycine). The invention therefore provides new methods for treating neuropsychiatric disorders in patients (i.e., humans). Examples of disorders that can be treated by the methods of the invention include schizophrenia, Alzheimer's Disease, autism, depression, benign forgetfulness, childhood learning disorders, close head injury, and attention deficit disorder. The methods entail administering to a patient diagnosed as suffering from such a neuropsychiatric disorder a-pharmaceutical composition that contains a therapeutically effective amount of an agonist of the glycine site of the NMDA receptor or a glycine uptake inhibitor, which agonist is relatively selective for (a) the glycine site of the NMDA receptor, compared with (b) the inhibitory glycine receptor and other receptors. The pharmaceutical composition may include, for example, (i) a therapeutically effective amount of D-alanine (wherein the pharmaceutical composition is substantially free of D-cycloserine) and/or (ii) a therapeutically effective amount of D-serine, and/or (iii) D-cycloserine in an amount of 105–500 mg, and/or (iv) a therapeutically effective amount of N-methylglycine.

In variations of the methods described herein, D-serine, D-alanine, D-cycloserine, and/or N-methylglycine can be substituted with a salt, ester, or alkylated form of the amino acid, or a precursor of the amino acid that is converted (e.g., metabolized) into the amino acid in vivo (e.g., D-phosphoserine, L-phosphoserine, or L-phosphoserine, N,N,N-trimethylglycine (betaine), or N,N-dimethylglycine).

Typically, a dosage of 100 μg to 100 g (e.g., 1 mg to 100 g; 1 mg to 100 mg; 10 mg to 100 g; 10 mg to 10 g; or 10 to 500 mg) is suitable for D-alanine, D-serine, and N-methylglycine. D-cycloserine is administered at a dosage of 105 to 500 mg. When the patient is treated with both D-serine and D-alanine, D-serine and D-alanine can be administered to the patient simultaneously or sequentially, e.g., by formulating the D-serine and D-alanine as a single pharmaceutical composition or as two or more pharmaceutical compositions. Likewise, the patient can be treated with both D-serine and D-cycloserine, or D-serine and N-methylglycine, or D-alanine and N-methylglycine, or D-cycloserine and N-methylglycine simultaneously or sequentially. In one, but not the only, suitable method of treatment, the pharmaceutical composition is administered to the patient at least once daily for at least one week. If desired, the pharmaceutical composition can be administered to the patient in more than one dose per day (e.g., 2, 3, or 4 doses). Generally, the patient is treated for at least one week; typically, the patient is treated for at least several weeks (e.g., at least 4, 6, or 8 weeks) or months (e.g., at least 4, 8, or 12 months). If necessary, the treatment can continue indefinitely to keep the patient's symptoms under control throughout his or her life.

If desired, a pharmaceutical composition containing D-alanine (substantially free of D-cycloserine), D-serine, D-cycloserine and/or N-methylglycine (or a modified version thereof, as described herein) can be administered to a patient suffering from schizophrenia along with, or in sequence with, an art-known drug for treating schizophrenia (e.g., olanzapine, clozapine, haloperidol, and the like). Similarly, D-alanine (typically substantially free of D-cycloserine), D-serine, D-cycloserine and/or N-methylglycine (or a modified version thereof, as described herein) can be used in combination with, or in sequence with, other art-known antipsychotics (e.g., "typical," "a typical," and depot antipsychotics for treating schizophrenia and other psychotic conditions), antidepressants (for treating depression), psychostimulants (for treating attention deficit disorder, depression, or learning disorders), or Alzheimer's disease therapeutics (for treating Alzheimer's disease). Such pharmaceutical compositions are included within the invention. In general, the antipsychotic, antidepressant, psychostimulant, or Alzheimer's disease therapeutic typically is administered at a dosage of 0.25–5000 mg/d (e.g., 5–1000 mg/d)). "Typical" antipsychotics are conventional antipsychotics such as phenothiazine, butryophenones, thioxantheses, dibenzoxazepines, dihydroindolones, and diphenylbutylpiperidines. "Atypical", antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics (and examples of suitable daily (d) dosages) include Chlorpromazine (5–2000 mg/d, e.g., 30–800 mg/d), Thioridazine (5–2000 mg/d, e.g., 20–800 mg/d), Mesoridazine (1–1000 mg/d, e.g., 30–400 mg/d), Fluphenazine (0.5–200 mg/d, e.g., 1–40 mg/d), Perphenazine (0.5–300 mg/d, e.g., 10–65 mg/d), Trifluoperazine (0.5–200 mg/d, e.g., 2–40 mg/d), Thiothixene (1–200 mg/d, e.g., 6–60 mg/d), Haloperidol (0.25–500 mg/d, e.g., 1–100 mg/d), Loxapine (1–1000 mg/d e.g., 20–250 mg/d), Molindone (1–1000 mg/d, e.g., 15–225 mg/d), Acetophenazine (10–2000 mg/d, e.g., 30–500 mg/d), Chlorprothixene (5–2000 mg/d, e.g., 30–500 mg/d), Droperidol (0.25–500 mg/d, e.g., 1–100 mg/d), Pimozide (0.25–500 mg/d, e.g., 1–100 mg/d). Examples of a typical antipsychotics (and examples of suitable daily dosages) include Clozapine (5–2000 mg/d, e.g., 12–900 mg/d), Risperidone (0.25–500 mg/d, e.g., 2–16 mg/d), Olanzapine (1–100 mg/d, e.g., 5–10 mg/d), and Quetiapine (1–2000 mg/d, e.g., 50–750 mg/d). Depot antipsychotics also can be used, e.g., Haloperidol decanoate (10–1000 mg/month, e.g., 100–450 mg/month), Fluphenazine decanoate (5–1000 mg/month, e.g., 25–150 mg/month), and Fluphenazine enanthate (5–1000 mg/month, e.g., 25–200 mg/month). Additional antipsychotics include Butaperazine (0.5–500 mg/d, e.g., 1–200 mg/d), Carphenazine, (0.5–3000 mg/d, e.g., 1–1000 mg/d), Remoxipride (0.5–5000 mg/d, e.g., 1–2000 mg/d), Piperacetazine (0.5–500 mg/d, e.g., 1–2000 mg/d), Sulpiride (~0.5–5000-mg/d, e.g., 1–2000 mg/d), and Ziprasidone (0.5–500 mg/d, e.g., 1–200 mg/d). Examples of antidepressants that can be used include Amitriptyline (5–1000 mg/d, e.g., 50–300 mg/d), Amoxapine (5–1000 mg/d, e.g., 50–600 mg/d), Bupropion (5–1000 mg/d, e.g., 200–450 mg/d), Bupropion SR (5–1000 mg/d, e.g., 150–400 mg/d), Clomipramine (5–1000 mg/d, e.g., 25–250 mg/d), Desipramine (5–1000 mg/d, e.g., 100–300 mg/d), Doxepin (5–1000 mg/d, e.g., 75–300 mg/d), Fluoxetine (1–200 mg/d, e.g., 20–80 mg/d), Fluvoxamine (5–1000 mg/d, e.g., 50–300 mg/d), Imipramine (5–1000 mg/d, e.g., 75–300 mg/d), Maprotiline (5–1000, e.g., 75–225 mg/d), Mirtazapine (1–200 mg/d, e.g., 15–45 mg/d), Nefazodone (5–1000 mg/d, e.g., 200–600 mg/d), Nortriptyline (5–1000 mg/d, e.g., 75–150 mg/d), Paroxetine (1–200 mg/d, e.g., 10–60 mg/d), Phenelzine (1–500 mg/d, e.g., 5–90 mg/d), Protriptyline (1–200 mg/d, e.g., 15–60 mg/d), Sertraline (5–1000 mg/d, e.g., 50–200 mg/d), Tranylcypromine (1–200 mg/d, e.g., 30–60 mg/d), Trazodone (5–1000 mg/d, e.g., 150–600 mg/d), Trimipramine (5–1000 mg/d, e.g., 5–300 mg/d), Venlafaxine (5–1000 mg/d, e.g., 75–375 mg/d), and Venlafaxine XR (5–1000 mg/d, e.g, 75–225 mg/d). Psychostimulants that are particularly useful for treating attention deficit disorder include Dextroamphetamine (0.5–200 mg/d, e.g., 5–40 mg/d), Methamphetamine (0.5–200 mg/d, e.g., 5–25 mg/d), Methylphenidate (0.5–200 mg/d, e.g., 10–40 mg/d), and Pemoline (5–500 mg/d, e.g., 37.5–112.5 mg/d). Examples of Alzheimer's disease therapeutics that can be used in the invention include Donepezil (0.5–200 mg/d, e.g., 1–100 mg/d) and Tacrine (0.5–1000 mg/d, e.g., 10–500 mg/d). Thus, the invention also provides pharmaceutical compositions that contain D-alanine (typically substantially free of D-cycloserine), D-serine, D-cycloserine and/or N-methylglycine (or a modified version thereof, as described herein) along with an antipsychotic, antidepressant, psychostimulant, or Alzheimer's disease therapeutic.

If desired, one can measure negative and/or positive and/or cognitive symptom(s) of schizophrenia before and after treatment of the patient. A reduction in such a symptom indicates that the patient's condition has improved. Improvement in the symptoms of schizophrenia can be assessed using the Scales for the Assessment of Negative Symptoms (SANS) or Positive and Negative Syndrome Scale (PANSS) (see, e.g., Andreasen, 1983, *Scales for the Assessment of Negative Symptoms (SANS)*, Iowa City, Iowa and Kay et al., 1987, Schizophrenia Bulletin 13:261–276). Likewise, one can measure improvement of other neuropsychiatric disorders in patients who have been treated by the methods of the invention.

As used herein, the term "neuropsychiatric disorder" refers to a disease having a pathophysiological component of attenuated NMDA receptor-mediated neurotransmission. Examples of such disorders include schizophrenia, Alzheimer's disease, autism, depression, benign forgetfulness, childhood learning disorders, close head injury, and attention deficit disorder.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSM-IV criteria (APA, 1994, *Diagnostic and Statistical Manual of Mental Disorders* (Fourth Edition), Washington, D.C.).

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing!Alzheimer's Disease are known in the art. For example, the National Institute of Neurological and Communicative Disorders and Stroke-Alzheimer's Disease-and the Alzheimer's Disease and Related Disorders Association (NINCDS-ADRDA) criteria can be used to diagnose Alzheimer's Disease (McKhann et al., 1984, Neurology 34:939–944). The patient's cognitive function can be assessed by the Alzheimer's Disease Assessment Scale-cognitive subscale (ADAS-cog; Rosen et al., 1984, Am. J. Psychiatry 141:1356–1364).

As used herein, the term "autism" refers to a state of mental introversion characterized by morbid self-absorption, social failure, language delay, and stereotyped behavior. Patients can be diagnosed as suffering from autism by using the DSM-IV criteria.

As used herein, the term "depression" refers to a clinical syndrome that includes a persistent sad mood or loss of interest in activities, which lasts for at least two weeks in the absence of treatment. The DSM-IV criteria can be used to diagnose patients as suffering from depression.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40-years of age and can be recognized by standard assessment instruments such as the Wechsler Memory Scale (Russell, 1975, J. Consult Clin. Psychol. 43:800–809).

As used herein, the term "childhood learning disorders" refers to an impaired ability to learn, as experienced by certain children. Such learning disorders can be diagnosed by using the DSM-IV criteria.

The term "close head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to a disorder that is most commonly exhibited by children and which can be characterized by increased motor activity and a decreased attention span. The DSM-IV criteria can be used to diagnose attention deficit disorder.

The terms "D-serine" and "D-alanine" refer to the D isomers of the amino acids serine and alanine, respectively. As D isomers, rather than L isomers, these amino acids are not naturally found in proteins.

"Negative" symptoms of schizophrenia include affect blunting, anergia, alogia and social withdrawal, which can be measured using SANS (the Scales for the Assessment of Negative Symptoms; see Andreasen, 1983, *Scales for the Assessment of Negative Symptoms (SANS)*, Iowa City, Iowa).

"Positive" symptoms of schizophrenia include delusion and hallucination, which can be measured using PANSS (the Positive and Negative Syndrome Scale; see Kay et al., 1987, Schizophrenia Bulletin 13:261–276).

"Cognitive" symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, J. Nerv. Ment. Dis. 182:631–638) or with cognitive tasks such as the Wisconsin Card Sorting Test.

A "full" agonist of the NMDA receptor is a compound that produces a maximal response at full receptor occupancy.

A "partial" agonist of the NMDA receptor is a compound that produces a lower maximal response at full receptor occupancy than do full agonists.

A "glycine uptake inhibitor of the NMDA receptor" is a compound that inhibits the re-uptake of glycine and increases the availability of glycine for the NMDA receptor (e.g., N-methylglycine).

The invention offers several advantages over many art-known methods for treating neuropsychiatric disorders. For example, unlike many conventional antipsychotic therapeutics, D-serine, D-alanine, and N-methylglycine can produce a desirable reduction in the positive, negative, and cognitive symptoms of schizophrenia. As shown by the examples set forth below, clinically significant improvement can be achieved even with patients who are poorly responsive to treatment by conventional antipsychotics. In addition, no significant side effects were detected after treatment of schizophrenia patients with D-serine, D-alanine, or N-methylglycine. In contrast, conventional antipsychotics typically lead to tardive dyskinesia (irreversible, involuntary movement disorder), extrapyramidal symptoms, and akathesia symptoms.

Other features and advantages of the invention will be apparent from the following detailed-description, and from the claims.

DETAILED DESCRIPTION

The invention provides methods for treating a patient diagnosed as suffering from a neuropsychiatric disorder having a deficit in neurotransmission via the NMDA receptor (e.g., schizophrenia, Alzheimer's Disease, autism, depression, benign forgetfulness, childhood learning disorders, close head injury, and attention deficit disorder). As described above, a variety of methods for diagnosing these disorders are known to those of skill in the art of clinical psychiatry, and any conventional diagnostic method can be used in conjunction with the invention.

The treatment method of the invention entails administering to a patient diagnosed as having a neuropsychiatric disorder a pharmaceutical composition containing a therapeutically effective amount of (i) an agonist of the glycine site of the NMDA receptor, which agonist is relatively selective for (a) the glycine site of the NMDA receptor, compared with (b) an inhibitory glycine receptor or any other receptor, or (ii) a glycine uptake inhibitor. For example, suitable pharmaceutical compositions may include (i) D-alanine substantially free of D-cycloserine and/or (ii) D-serine and/or (iii) N-methylglycine. D-serine and D-alanine are commercially available (e.g., from Spectrum Quality Products, Inc., Gardena, Calif.). Where D-alanine is used, the pharmaceutical composition is "substantially free" of D-cycloserine, meaning that the composition lacks D-cycloserine, or D-cycloserine is not included at a level sufficient to have a statistically significant effect upon the efficacy of the pharmaceutical composition, as determined by any method (e.g., by comparing PANSS and/or SANS scores before and after treatment of the patient). In general, this means that D-cycloserine is absent from the pharmaceutical composition or present in an amount such that the patient receives less than 0.02 mg/day.

Treatment includes administering a therapeutically effective amount of a composition containing D-alanine (substantially free of D-cycloserine) and/or D-serine and/or N-methylglycine to a patient in need of such treatment, thereby treating the neuropsychiatric disorder. Such compositions typically contain from about 0.1 to 90% by weight (such as 1 to 20% or 1 to 10%) of D-alanine, D-serine, or N-methylglycine in a pharmaceutically acceptable carrier. Regardless of the concentration of D-serine or D-alanine in the pharmaceutical composition, D-serine and/or D-alanine and/or N-methylglycine is administered to the patient at a dosage of 10 mg to 100 g. More typically, D-serine and/or D-alanine and/or N-methylglycine is administered at a dosage of 100 mg to 10 g. Generally, treatment continues for at least several weeks to several years or life-long as needed.

In an alternative method for treating a neuropsychiatric disorder in a patient, a pharmaceutical composition containing D-cycloserine in an amount equivalent to a dosage of 105 to 500 mg/day is administered to a patient in need of such treatment. For example, the dosage can be in an amount of 125 to 400 mg, such as 150 to 300 mg (e.g., 175 mg, 200 mg, 225 mg, or 250 mg). D-cycloserine (D-4-amino-3-isoxazolidinone) is commercially available from Eli Lilly, Inc. (Indianapolis, Ind.). Generally, treatment continues for at least one week and can continue for several years or life-long as needed to control the patient's symptoms.

In all of the methods of the invention, D-alanine, D-serine, and/or D-cycloserine and/or N-methylglycine can be substituted with a modified version of the amino acid, such as a salt, ester, alkylated form, or a precursor of the amino acid. For example, the amino acid can be in the form of a sodium salt, potassium salt, calcium salt, magnesium salt, zinc salt, or ammonium salt. Such salt forms of D-serine, D-alanine, N-methylglycine and D-cycloserine can be made in accordance with conventional methods (see, e.g., *Organic Chemistry,* pgs. 822–823, Morrison and Boyd, ed., Fifth Edition, Allyn and Bacon, Inc., Newton, Mass.). Other modified forms of D-serine, D-alanine, N-methylglycine and D-cycloserine also can be used in the methods of the invention. For example, the carboxy group of the amino acid can be converted to an ester group by reaction with an alcohol in accordance with standard esterification methods (Id. at 841–843). For example, alcohols having 1–20 carbon atoms can be used to produce an ester of D-serine, D-alanine, N-methylglycine or D-cycloserine for use in the invention (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl-, and phenyl- alcohols can be used). In another variation, the amino group of the amino acid can be alkylated, using conventional methods, to produce a secondary or tertiary amino group by ammonolysis of halides or reductive amination (Id. at 939–948). For example, an alkyl group having 1–20 carbon atoms can be added to the amino acid to produce an alkylated amino acid (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl- and phenyl- groups can be added to the amino acid). D-phosphoserine and L-phosphoserine are examples of precursors of D-serine, and are commercially available (e.g., from Sigma Chemical, St. Louis, Mo.). N,N,N-trimethylglycine (betaine) and N,N-dimethylglycine are examples of precursors of N-methylglycine.

In all of the methods of the invention, appropriate dosages of D-alanine, D-serine, D-cycloserine, or N-methylglycine (or modified versions thereof) can readily be determined by those of ordinary skill in the art of medicine by monitoring the patient for signs of disease amelioration or inhibition, and increasing or decreasing the dosage and/or frequency of treatment as desired.

The pharmaceutical compositions can be administered to the patient by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

EXAMPLES

The following examples demonstrate that D-alanine, D-serine, and N-methylglycine each can be used to treat a neuropsychiatric disorder in patients.

Patients

This study employed 37 patients who were diagnosed as having schizophrenia. All patients fulfilled the DSM-IV diagnosis of schizophrenia (APA, 1994, Diagnostic and Statistical Manual of Mental Disorders, Fourth Edition, Washington, D.C.). All of the patients also fulfilled the criteria of primary deficit syndrome, with a SANS score of more than 40 (Kirkpatrick et al., 1989, Psychiatry Research 30:119–123; Andreasen, 1983, Scales for the Assessment of Negative Symptoms (SANS), Iowa City, Iowa). All of the patients were poorly responsive to treatment by other antipsychotic drugs, and had been kept on a stable dose of an antipsychotic drug for at least 3 months prior to enrollment in this study.

Assessments

Several scales were used to assess the severity of the disorder in each patient. At the beginning of the study (i.e., the baseline), the PANSS, SANS, and Global Assessment Scales (CGI) were used. Each scale also was completed at the end of each 2-week period throughout the study. These assessments were performed by a psychiatrist who was blind to the treatment assignment. The Wisconsin Card Sort Test was used to provide a cognitive rating of the patients; in general, schizophrenic patients perform poorly on this test. The Wisconsin Card Sort Test was administered only at the initiation of the study and at the end of the 6-week study. To measure side effects, the Simpson-Angus Scale was used to measure extrapyramidal symptoms (EPS; Simpson et al., 1970, Acta Psychiatrica Scandinavia Suppl. 212:11–19). The Abnormal Involuntary Movement Scale (AIMS) was used to measure dyskinesia (Simpson et al., 1970, Acta Psychiatrica Scandinavia Suppl. 212:11–19). The Barnes Scale was used to measure akathesia (Barnes, 1989, Brit. J. Psychiatry 154:672–676). The side effects of D-serine, D-alanine, and N-methylglycine treatments were assessed biweekly according to the UKU side effects rating scale (*Scandinavian Society of Psychopharmacology Committee of Clinical Investigation: The UKU side effect rating scale: scale for the registration of unwanted effects of psychotropics.* Acta. Psychiatr. Scand. 1987; Suppl. 334:81–94).

Treatment and Results

Using double-blind conditions, the patients were randomly assigned to receive placebo (fruit juice), D-serine (30 mg/kg/day), D-alanine (60–100 mg/kg/day), or N-methylglycine (30 mg/kg/day) once a day by mouth for a period of 6 weeks. As indicated by the results shown in Table 1, treatment with D-serine, D-alanine, or N-methylglycine improved the schizophrenic symptoms and cognitive deficit of the patients. More specifically, treatment with D-serine resulted in a 21% reduction of the negative symptoms (on the SANS scale), and it resulted in a 17% reduction of the positive symptoms (on the PANSS-positive subscale). Treatment with D-alanine resulted in an 11% reduction of the negative symptoms and a 12% reduction of the positive symptoms. Treatment with N-methylglycine resulted in a 20% reduction of the negative symptoms and a 15% reduction of the positive symptoms. These reductions in the negative and positive symptoms represented clinically significant improvement. Treatment with each of D-serine, D-alanine, and N-methylglycine also improved cognition, as measured using the PANSS-cognitive subscale and the Wisconsin Card Sort Test. These results indicate that D-serine, D-alanine, and N-methylglycine are effective in treating schizophrenia even in patients who are poorly responsive to treatment by conventional-antipsychotic drugs.

Using the UKU scale for rating side effects, no side effects were noted after treatment with D-serine, D-alanine, or N-methylglycine. In addition, there was no newly emergent tardive dyskinesia or worsening of extrapyramidal or akathesia symptoms. Thus, D-serine, D-alanine, and N-methylglycine offer an advantage over many conventional drugs for treating schizophrenia in that they do not cause significant side effects.

TABLE 1

Effects of D-serine, D-alanine, and N-methylglycine Treatment on Schizophrenia Patients

| Clinical Symptoms | D-serine | D-alanine | N-methyl-glycine | Placebo |
| --- | --- | --- | --- | --- |
| Negative Symptoms | −21%* | −12%* | −20%* | −1% |
| Positive Symptoms | −17%* | −11%* | −15%* | 3% |
| CGI | 4.8 -> 2.6* | 3.9 -> 2.8* | 4.2 -> 2.7* | 4.5 -> 4.0 |
| Cognition | | | | |
| Cognitive symptoms | −12%* | −%* | −12%* | 1% |
| WCST | +0.9 (category)* | +0.5* | +0.7* | −0.5 |
| Side Effects | | | | |
| EPS | 1.4 -> 1.7 | 3.1 -> 3.1 | 2.1 -> 2.1 | 3.3 -> 3.4 |
| AIMS | 0.3 -> 0.3 | 0.5 -> 0.1 | 0.4 -> 0.3 | 0.5 -> 0.9 |
| Barnes | 0.4 -> 0.8 | 0.4 -> 0.6 | 0.5 -> 0.6 | 0.9 -> 0.9 |

*Clinically significant improvement

Other Embodiments

It is to be understood that, while the invention has been described in conjunction with the detailed description thereof, the foregoing description is intended to illustrate and not limit the scope of the invention, which is defined by the appended claims. Other aspects, advantages, and modifications are within the scope of the following claims.

What is claimed is:

1. A method for treating autism, the method comprising administering to a patient diagnosed as suffering from autism a pharmaceutical composition comprising a therapeutically effective amount of a compound selected from the group consisting of D-alanine, a salt of D-alanine, an ester of D-alanine, an alkylated D-alanine, a precursor of D-alanine, D-serine, a salt of D-serine, an alkylated D-serine, a precursor of D-serine, D-cycloserine, a salt of D-cycloserine, an ester of D-cycloserine, a precursor of D-cycloserine, an alkylated D-cycloserine, N-methylglycine, a salt of N-methylglycine, an ester of N-methylglycine, an alkylated N-methylglycine, and N,N,N-trimethylglycine.

2. The method of claim 1, wherein the compound is selected from the group consisting of D-alanine, a salt of D-alanine, an ester of D-alanine, an alkylated D-alanine, and a precursor of D-alanine.

3. The method of claim 2, wherein the D-alanine, salt of D-alanine, ester of D-alanine, alkylated D-alanine, or precursor of D-alanine is administered at a dosage equivalent to 10 mg to 100 g of D-alanine.

4. The method of claim 2, wherein the compound is a D-alanine salt selected from the group consisting of a sodium salt, a potassium salt, a calcium salt, a magnesium salt, a zinc salt, and an ammonium salt of D-alanine.

5. The method of claim 2, wherein the compound is an ester of D-alanine having an ester group with 1–20 carbon atoms.

6. The method of claim 2, wherein the compound is an alkylated D-alanine having an alkyl group with 1–20 carbon atoms.

7. The method of claim 2, wherein the pharmaceutical composition further comprises D-serine.

8. The method of claim 1, wherein the compound is selected from the group consisting of D-serine, a salt of D-serine, alkylated D-serine, and a precursor of D-serine.

9. The method of claim 8, wherein the D-serine, salt of D-serine, precursor of D-serine, or alkylated D-serine is administered at a dosage equivalent to 10 mg to 100 g of D-serine.

10. The method of claim 8, wherein the compound is a D-serine salt selected from the group consisting of a sodium salt, a potassium salt, a calcium salt, a magnesium salt, a zinc salt, and an ammonium salt of D-serine.

11. The method of claim 8, wherein the compound is an alkylated D-serine having an alkyl group with 1–20 carbon atoms.

12. The method of claim 1, wherein the compound is selected from the group consisting of D-cycloserine, a salt of D-cycloserine, an ester of D-cycloserine, a precursor of D-cycloserine, and an alkylated D-cyclosenne.

13. The method of claim 12, wherein the D-cycloserine, salt of D-cycloserine, ester of D-cycloserine, alkylated D-cycloserine, or precursor of D-cycloserine is administered in a dose equivalent to 125–400 mg of D-cycloserine.

14. The method of claim 13, wherein the D-cycloserine, D-cycloserine salt, ester of D-cycloserine, alkylated D-cycloserine, or precursor of D-cycloserine is administered in a dose equivalent to 150–300 mg of D-cycloserine.

15. The method of claim 12, wherein the compound is a salt of D-cycloserine selected from the group consisting of a sodium salt, a potassium salt, a calcium salt, a magnesium salt, a zinc salt, and an animonium salt of D-cyclosenne.

16. The method of claim 12, wherein the compound is an ester of D-cycloserine having an ester group with 1–20 carbon atoms.

17. The method of claim 12, wherein the compound is an alkylated D-cycloserine having an alkyl group with 1–20 carbon atoms.

18. The method of claim 12, wherein the compound is a precursor of D-cycloserine.

19. The method of claim 1, wherein the N-methylglycine, salt of N-methylglycine, ester of N-methylglycine, alkylated N-methylglycine, or N,N,N-trimethylglycine is administered at a dosage equivalent to 10 mg to 100 g of N-methylglycine.

20. The method of claim 1, wherein the compound is an ester of N-methylglycine having an ester group with 1–20 carbon atoms.

21. The method of claim 1, wherein the compound is an alkylated N-methylglycine having an alkyl group with 1–20 carbon atoms.

22. The method of claim 1, wherein the pharmaceutical composition is administered to the patient at least once daily for at least one week.

23. The method of claim 1, further comprising administering to the patient at least one therapeutic agent selected from the group consisting of antipsychotics, antidepressants, psychostimulants, and Alzheimer's disease therapeutics.

24. The method of claim 1, wherein the compound is a precursor of D-serine, and the precursor is D-phosphoserine or L-phosphoserine.

25. The method of claim 1, further comprising administering to the patient at least one therapeutic agent selected from the group consisting of Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Amitriptyline, Amoxapine, Bupropion, Bupropion SR, Clomipramine, Desipramine, Doxepin, Fluoxetine, Fluvoxamine, Imipramine, Maprotiline, Mirtazapine, Nefazodone, Nortriptyline, Paroxetine, Pheneizine, Protriptyline, Sertraline, Tranylcypromine, Trazodone, Trimipramine, Venlafaxine, Venlafaxine XR, Dextroamphetamine, Methamphetamine, Methylphenidate, Pemoline, Donepezil, Tacrine, Acetophenazine, Chlorprothixene, Droperidol, Pimozide, Butaperazine, Carphenazine, Remoxipride, Piperacetazine, Sulpiride, and Ziprasidone.

26. The method of claim 1, wherein the pharmaceutical composition is administered for at least six weeks.

27. The method of claim 1, wherein the pharmaceutical composition is administered for at least eight weeks.

28. The method of claim 1, wherein the pharmaceutical composition is administered for at least four months.

29. The method of claim 1, wherein the pharmaceutical composition is administered for at least eight months.

30. The method of claim 1, wherein the pharmaceutical composition is administered for at least twelve months.

31. A method for treating schizophrenia, the method comprising administering to a patient diagnosed as suffering from schizophrenia a pharmaceutical composition comprising a compound selected from the group consisting of D-serine, a salt of D-serine, an ester of D-serine, an alkylated D-serine, and a precursor of D-serine, wherein the pharmaceutical composition is administered at a dose equivalent to 100 mg to 10 g D-serine per day.

32. The method of claim 31, wherein the compound is D-serine.

33. The method of claim 31, wherein the compound is a salt of D-serine selected from the group consisting of a sodium salt, a potassium salt, a calcium salt, a magnesium salt, a zinc salt, and an ammonium salt of D-serine.

34. The method of claim 31, wherein the compound is an ester of D-serine having an ester group with 7, 8, 10, 12, 14, 16, or 18 carbon atoms.

35. The method of claim 31, wherein the compound is an alkylated D-serine having an alkyl group with 1–20 carbon atoms.

36. The method of claim 31, wherein the compound is a precursor of D-serine, and the precursor is D-phosphoserine or L-phosphoserine.

37. The method of claim 31, further comprising administering to the patient at least one therapeutic agent selected from the group consisting of antipsychotics, antidepressants, psychostimulants, and Alzheimer's disease therapeutics.

38. The method of claim 31, further comprising administering to the patient at least one therapeutic agent selected from the group consisting of Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Amitriptyline, Amoxapine, Bupropion, Bupropion SR, Clomipramine, Desipramine, Doxepin, Fluoxetine, Fluvoxamine, Imipramine, Maprotiline, Mirtazapine, Nefazodone, Nortriptyline, Paroxetine, Phenelzine, Protriptyline, Sertraline, Tranylcypromine, Trazodone, Trimipramine, Venlafaxine, Venlafaxine XR, Dextroamphetamine, Methamphetamine, Methylphenidate, Pemoline, Donepezil, Tacrine, Acetophenazine, Chlorprothixene, Droperidol, Pimozide, Butaperazine, Carphenazine, Remoxipride, Piperacetazine, Sulpiride, and Ziprasidone.

39. The method of claim 31, wherein the pharmaceutical composition is administered to the patient at least once daily for at least one week.

40. The method of claim 31, wherein the pharmaceutical composition is administered for at least six weeks.

41. The method of claim 31, wherein the pharmaceutical composition is administered for at least eight weeks.

42. The method of claim 31, wherein the pharmaceutical composition is administered for at least four months.

43. The method of claim 31, wherein the pharmaceutical composition is administered for at least eight months.

44. The method of claim 31, wherein the pharmaceutical composition is administered for at least twelve months.

45. A method for treating a positive symptom of schizophrenia, the method comprising administering to a patient diagnosed as suffering from a positive symptom of schizophrenia a pharmaceutical composition comprising a therapeutically effective amount of a compound selected from the group consisting of D-serine, a salt of D-serine, an ester of D-serine, an alkylated D-serine, and a precursor of D-serine.

46. The method of claim 45, further comprising observing an improvement in the patient's positive symptom following administration of the pharmaceutical composition.

47. The method of claim 46, wherein the compound is D-serine.

48. The method of claim 46, wherein the compound is a salt of D-serine selected from the group consisting of a sodium salt, a potassium salt, a calcium salt, a magnesium salt, a zinc salt, and an ammonium salt of D-serine.

49. The method of claim 46, wherein the compound is an ester of D-serine having an ester group with 1–20 carbon atoms.

50. The method of claim 46, wherein the compound is an alkylated D-serine having an alkyl group with 1–20 carbon atoms.

51. The method of claim 46, wherein the compound is a precursor of D-serine, and the precursor is D-phosphoserine or L-phosphoserine.

52. The method of claim 46, further comprising administering to the patient at least one therapeutic agent selected from the group consisting of antipsychotics, antidepressants, psychostimulants, and Alzheimer's disease therapeutics.

53. The method of claim 46, further comprising administering to the patient at least one therapeutic agent selected from the group consisting of Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Amitriptyline, Amoxapine, Bupropion, Bupropion SR, Clomipramine, Desipramine, Doxepin, Fluoxetine, Fluvoxamine, Imipramine, Maprotiline, Mirtazapine, Nefazodone, Nortriptyline, Paroxetine, Pheneizine, Protriptyline, Sertraline, Tranylcypromine, Trazodone, Trimipramine, Venlafaxine, Venlafaxine XR, Dextroamphetamine, Methamphetamine, Methylphenidate, Pemoline, Donepezil, Tacrine, Acetophenazine, Chiorprothixene, Droperidol, Pimozide, Butaperazine, Carphenazine, Remoxipride, Piperacetazine, Sulpiride, and Ziprasidone.

54. The method of claim 46, wherein the pharmaceutical composition is administered to the patient at least once daily for at least one week.

55. The method of claim 46, wherein the pharmaceutical composition is administered for at least six weeks.

56. The method of claim 46, wherein the pharmaceutical composition is administered for at least eight weeks.

57. The method of claim 46, wherein the pharmaceutical composition is administered for at least four months.

58. The method of claim 46, wherein the pharmaceutical composition is administered for at least eight months.

59. The method of claim 46, wherein the pharmaceutical composition is administered for at least twelve months.

* * * * *

UNITED STATES PATENT AND TRADEMARK OFFICE
CERTIFICATE OF CORRECTION

PATENT NO.      : 6,667,297 B2
DATED           : December 23, 2003
INVENTOR(S)     : Guochuan Tsai and Joseph Coyle It is certified that error appears in the above-identified patent and that said Letters Patent is hereby corrected as shown below:

Title page,
Item [56], References Cited, FOREIGN PATENT DOCUMENTS, delete
"DE    41 17 629    12/1992
EP     0 387 867    9/1990
JP     8-26986      1/1996".
OTHER PUBLICATIONS, "Jaitt et al." reference, replace "schzophrenia" with
-- schzophrenia --
"Ramakrishma" reference, replace "Ramakrishma" with -- Ramakrishna --

Column 11,
Line 28, replace "Pheneizine" with -- Phenelzine --.

Column 13,
Line 9, replace "Pheneizine" with -- Phenelzine --.
Line 14, replace "Chiorprothixene" with -- Chlorprothixene --.

Signed and Sealed this

Twenty-second Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,667,297 B2
DATED : December 23, 2003
INVENTOR(S) : Guochuan Tsai and Joseph Coyle It is certified that error appears in the above-identified patent and that said Letters Patent is hereby corrected as shown below:

Title page,
Item [56], References Cited, FOREIGN PATENT DOCUMENTS, delete
"DE    41 17 629    12/1992
 EP    0 387 867    9/1990
 JP    8-26986      1/1996".
OTHER PUBLICATIONS, "Jaitt et al." reference, replace "schzophrenia" with
-- schzophrenia --
"Ramakrishma" reference, replace "Ramakrishma" with -- Ramakrishna --
Add -- Patent Abstract; XP-002117996; "Antidepressant Drug Low Side Effect Contain Serine Salt Effect Component"; JP55020747A; 1980 --

Column 11,
Line 28, replace "Pheneizine" with -- Phenelzine --.

Column 13,
Line 9, replace "Pheneizine" with -- Phenelzine --.
Line 14, replace "Chiorprothixene" with -- Chlorprothixene --.

This certificate supersedes Certificate of Correction issued February 22, 2005.

Signed and Sealed this

Third Day of May, 2005

JON W. DUDAS
*Director of the United States Patent and Trademark Office*